(12) United States Patent
Shimada et al.

(10) Patent No.: US 10,509,215 B2
(45) Date of Patent: Dec. 17, 2019

(54) LIGHT-FIELD MICROSCOPE

(71) Applicant: OLYMPUS CORPORATION, Hachioji-shi, Tokyo (JP)

(72) Inventors: Yoshihiro Shimada, Kanagawa (JP); Yujin Arai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 297 days.

(21) Appl. No.: 15/436,738

(22) Filed: Feb. 17, 2017

(65) Prior Publication Data

US 2017/0261731 A1 Sep. 14, 2017

(30) Foreign Application Priority Data

Mar. 14, 2016 (JP) .................. 2016-049388

(51) Int. Cl.
*G02B 21/00* (2006.01)
*G01N 21/64* (2006.01)
*G02B 21/02* (2006.01)

(52) U.S. Cl.
CPC ..... *G02B 21/0032* (2013.01); *G01N 21/6458* (2013.01); *G02B 21/0048* (2013.01); *G02B 21/0072* (2013.01); *G02B 21/0076* (2013.01); *G02B 21/025* (2013.01); *G01N 2021/6478* (2013.01); *G01N 2201/0697* (2013.01); *G01N 2201/06113* (2013.01); *G01N 2201/10* (2013.01); *G01N 2201/105* (2013.01)

(58) Field of Classification Search
CPC ............ G02B 21/0032; G02B 21/0048; G02B 21/0076; G02B 21/0072; G01N 2201/6478; G01N 2201/10; G01N 2201/105; G01N 2201/0697

See application file for complete search history.

(56) References Cited

U.S. PATENT DOCUMENTS

| 6,711,283 | B1 * | 3/2004 | Soenksen | G02B 21/002 |
| | | | | 382/133 |
| 6,903,347 | B2 * | 6/2005 | Baer | G02B 21/0056 |
| | | | | 250/458.1 |
| 7,297,961 | B2 * | 11/2007 | Kang | G02B 21/16 |
| | | | | 250/458.1 |
| 7,554,725 | B2 * | 6/2009 | Stelzer | G02B 21/06 |
| | | | | 359/385 |
| 7,723,662 | B2 | 5/2010 | Levoy et al. | |

(Continued)

*Primary Examiner* — David P Porta
*Assistant Examiner* — Djura Malevic
(74) *Attorney, Agent, or Firm* — Holtz, Holtz & Volek PC

(57) ABSTRACT

The present invention provides a light-field microscope including: an illumination optical system that radiates excitation light onto a sample; and a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens. The illumination optical system radiates a beam of the excitation light having a predetermined width in the optical-axis direction of the objective lens so as to include the focal plane of the objective lens onto the sample in a direction substantially perpendicular to the optical axis.

23 Claims, 6 Drawing Sheets

(56) References Cited

U.S. PATENT DOCUMENTS

| | | | | |
|---|---|---|---|---|
| 7,787,179 B2* | 8/2010 | Lippert | G02B 21/06 | 359/385 |
| 7,801,352 B2* | 9/2010 | Uchiyama | G02B 21/367 | 382/133 |
| 8,351,120 B2* | 1/2013 | Deng | G02B 27/0012 | 348/241 |
| 8,441,633 B2* | 5/2013 | Truong | G01N 21/6408 | 356/301 |
| 8,792,162 B2* | 7/2014 | Lippert | G02B 21/0032 | 359/385 |
| 8,809,810 B2* | 8/2014 | Liu | G01N 21/6452 | 250/483.1 |
| 8,970,950 B2* | 3/2015 | Stelzer | G02B 21/06 | 359/385 |
| 8,978,984 B2* | 3/2015 | Hennick | G06K 7/10732 | 235/462.41 |
| 9,057,879 B2* | 6/2015 | Knebel | G02B 21/002 | |
| 9,110,301 B2* | 8/2015 | Lippert | G02B 21/002 | |
| 9,134,521 B2* | 9/2015 | Huisken | G02B 21/0048 | |
| 9,217,665 B2* | 12/2015 | Santori | G01J 1/0407 | |
| 9,305,956 B2* | 4/2016 | Pitts | H01L 27/14627 | |
| 9,307,169 B2* | 4/2016 | Kodama | G01J 3/0208 | |
| 9,500,849 B2* | 11/2016 | Lippert | G02B 21/002 | |
| 9,645,378 B2* | 5/2017 | Hilbert | G02B 21/002 | |
| 9,658,443 B2* | 5/2017 | Broxton | G02B 21/367 | |
| 9,678,323 B2* | 6/2017 | Orth | G02B 21/16 | |
| 9,697,605 B2* | 7/2017 | Lippert | G02B 21/002 | |
| 9,804,378 B2* | 10/2017 | Singer | G02B 27/0025 | |
| 9,810,896 B2* | 11/2017 | Nishiwaki | G02B 21/367 | |
| 9,829,691 B2* | 11/2017 | Otte | G02B 21/0032 | |
| 10,018,819 B2* | 7/2018 | Iguchi | G02B 21/06 | |
| 10,042,148 B2* | 8/2018 | Iguchi | G02B 21/006 | |
| 10,048,482 B2* | 8/2018 | Pretorius | G02B 27/0025 | |
| 10,114,207 B2* | 10/2018 | Ishiwata | G02B 21/361 | |
| 2003/0218746 A1* | 11/2003 | Sampas | G01N 21/6428 | 356/318 |
| 2005/0089208 A1* | 4/2005 | Dong | G02B 21/241 | 382/133 |
| 2005/0092934 A1* | 5/2005 | Kang | G02B 21/16 | 250/458.1 |
| 2006/0012872 A1* | 1/2006 | Hayashi | G01N 21/21 | 359/386 |
| 2006/0033987 A1* | 2/2006 | Stelzer | G02B 21/06 | 359/385 |
| 2006/0038144 A1* | 2/2006 | Maddison | G02B 21/367 | 250/559.05 |
| 2006/0088844 A1* | 4/2006 | Xu | C12Q 1/6825 | 435/6.12 |
| 2006/0197034 A1* | 9/2006 | Shirai | G01N 21/6428 | 250/458.1 |
| 2007/0035855 A1* | 2/2007 | Dickensheets | A61B 5/0068 | 359/819 |
| 2007/0058246 A1* | 3/2007 | Westphal | G02B 21/082 | 359/368 |
| 2007/0154938 A1* | 7/2007 | Oshida | G01N 21/6428 | 435/6.11 |
| 2007/0206097 A1* | 9/2007 | Uchiyama | G02B 21/367 | 348/207.99 |
| 2007/0206276 A1* | 9/2007 | Gugel | G02B 21/0076 | 359/385 |
| 2008/0185533 A1* | 8/2008 | Kimura | G02B 21/002 | 250/458.1 |
| 2009/0237765 A1* | 9/2009 | Lippert | G02B 21/06 | 359/213.1 |
| 2010/0111768 A1* | 5/2010 | Banerjee | C12Q 1/6869 | 422/82.08 |
| 2010/0148092 A1* | 6/2010 | Zheng | G01N 21/6452 | 250/459.1 |
| 2011/0115895 A1* | 5/2011 | Huisken | G02B 21/0048 | 348/79 |
| 2012/0098949 A1* | 4/2012 | Knebel | G02B 21/002 | 348/79 |
| 2012/0200693 A1* | 8/2012 | Lippert | G02B 21/002 | 348/79 |
| 2013/0130937 A1* | 5/2013 | Sun | G01N 21/6452 | 506/16 |
| 2013/0228705 A1* | 9/2013 | Nishikawa | G01N 15/1463 | 250/459.1 |
| 2015/0153560 A1* | 6/2015 | Lippert | G02B 21/367 | 348/79 |
| 2015/0168702 A1* | 6/2015 | Harris | G02B 21/08 | 850/30 |
| 2015/0168706 A1* | 6/2015 | Schweinitzer | G02B 21/367 | 348/80 |
| 2015/0177506 A1* | 6/2015 | Nishiwaki | G02B 21/367 | 348/46 |
| 2015/0253560 A1* | 9/2015 | Otte | G02B 21/0032 | 359/385 |
| 2015/0355449 A1* | 12/2015 | Orth | G02B 21/16 | 348/79 |
| 2016/0070091 A1* | 3/2016 | Hufnagel | G02B 21/0076 | 359/385 |
| 2016/0124201 A1* | 5/2016 | Kikuchi | G02B 21/16 | 359/385 |
| 2016/0124203 A1* | 5/2016 | Ryu | G02B 21/06 | 348/79 |
| 2016/0139394 A1* | 5/2016 | Taniguchi | G02B 21/24 | 359/385 |
| 2016/0154236 A1* | 6/2016 | Siebenmorgen | G02B 21/0032 | 359/385 |
| 2016/0170195 A1* | 6/2016 | Siebenmorgen | G02B 21/0032 | 359/385 |
| 2016/0291304 A1* | 10/2016 | Singer | G02B 27/0025 | |
| 2016/0305883 A1* | 10/2016 | Betzig | G02B 21/16 | |
| 2016/0306154 A1* | 10/2016 | Iguchi | G02B 21/06 | |
| 2016/0334613 A1* | 11/2016 | Ishiwata | G02B 21/361 | |
| 2017/0139193 A1* | 5/2017 | Iguchi | G02B 21/006 | |
| 2018/0088308 A1* | 3/2018 | Liu | G02B 21/367 | |

\* cited by examiner

LIGHT-FIELD MICROSCOPE

This application claims the benefit of Japanese Patent Application No. 2016-049388, the content of which is incorporated herein by reference.

TECHNICAL FIELD

The present invention relates to light-field microscopes.

BACKGROUND ART

A known light-field microscope in the related art can construct three-dimensional image data of a sample by performing a single image acquisition while focused on a deep part in the sample (for example, see PTL 1).

CITATION LIST

Patent Literature

{PTL 1} U.S. Pat. No. 7,723,662, Specification

SUMMARY OF INVENTION

An aspect of the present invention is a light-field microscope including: an illumination optical system that radiates excitation light onto a sample; and a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens. The illumination optical system radiates a beam of the excitation light having a predetermined width in the optical-axis direction of the objective lens so as to include the focal plane of the objective lens onto the sample in a direction substantially perpendicular to the optical axis.

Another aspect of the present invention is a light-field microscope comprising: an illumination optical system that radiates excitation light onto a sample; and a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens. The illumination optical system includes a sheet-illumination-light generator that generates a sheet-shaped beam extending parallel to a direction substantially perpendicular to the optical axis of the objective lens and that radiates the beam onto the sample in a direction substantially perpendicular to the optical axis, and a scanner that scans the sheet-shaped beam generated by the sheet-illumination-light generator in the optical axis direction, over a predetermined area including the focal plane of the objective lens, within the exposure time for one image in the image-acquisition element.

DESCRIPTION OF EMBODIMENTS

A light-field microscope 1 according to a first embodiment of the present invention will be described below with reference to FIG. 1.

Figure 1:
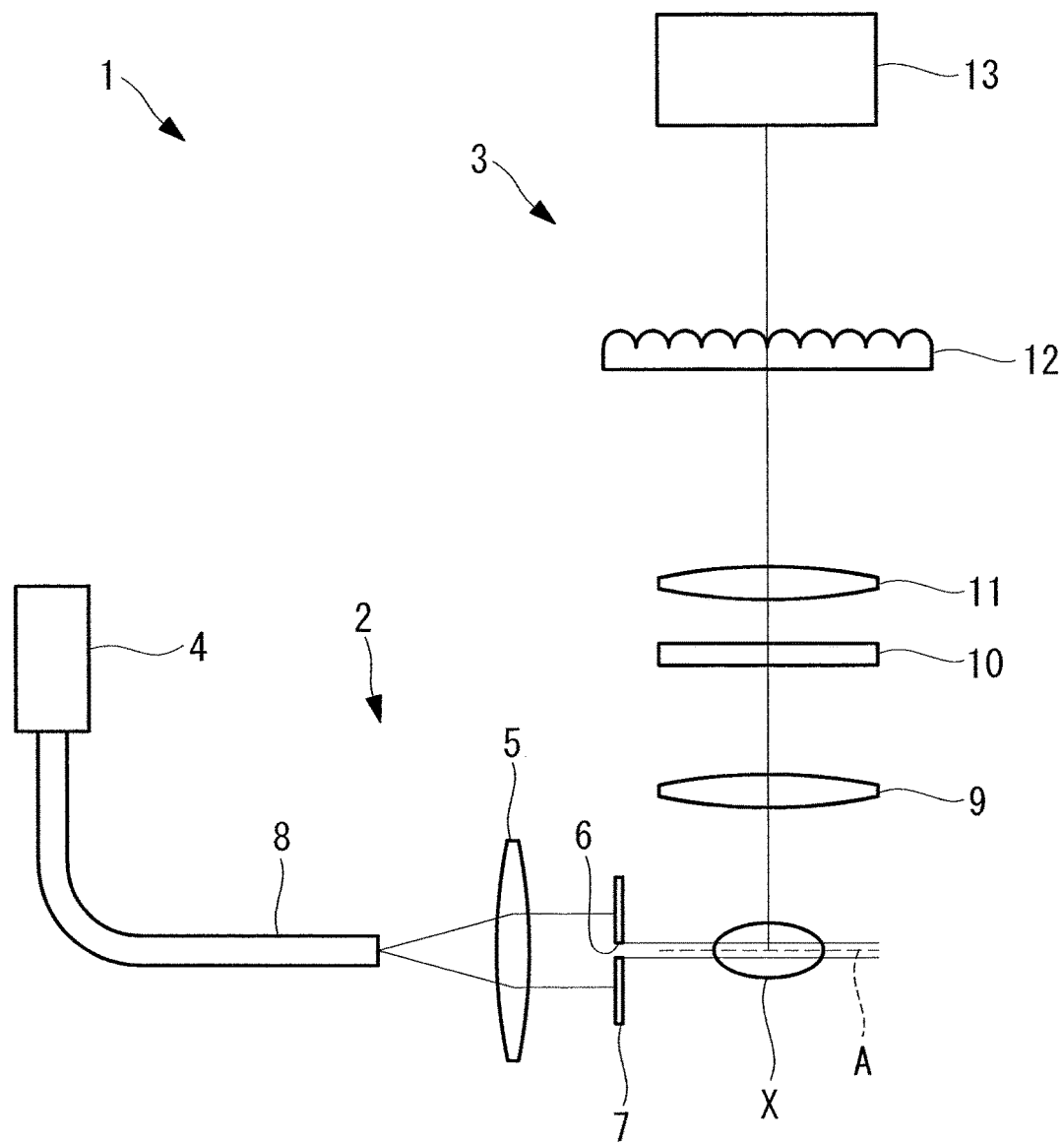
FIG. 1 is a schematic diagram showing the overall configuration of a light-field microscope according to a first embodiment of the present invention.

As shown in FIG. 1, the light-field microscope 1 according to this embodiment includes an illumination optical system 2 that radiates excitation light onto a sample X mounted on a stage (not shown), and a detection optical system 3 that detects fluorescence generated in the sample X.

The illumination optical system 2 includes a light source 4 that generates excitation light, a collimating lens 5 that substantially collimates the excitation light emitted from the light source 4, and a slit member (beam-width adjuster) 7 having a slit 6 that allows a portion of the excitation light substantially collimated by the collimating lens 5 to pass therethrough. In FIG. 1, reference sign 8 denotes an optical fiber for guiding the excitation light.

The excitation light emitted from the exit end of the optical fiber 8 is formed in a planar shape having a certain thickness delimited by the opening width of the slit 6 and is radiated onto the sample X, along a focal plane A of the objective lens 9 (described below).

The thickness of the excitation light is set to be slightly larger than the three-dimensional-image depth determined by the combination of the objective lens 9 and a microlens array 12 (described below).

The detection optical system 3 includes the objective lens 9 that has the optical axis perpendicular to the excitation-light incident direction and that collects fluorescence generated in the sample X, an emission filter 10 that removes the excitation light contained in the fluorescence collected by the objective lens 9, an image-forming lens 11 that focuses the fluorescence having passed through the emission filter 10, a microlens array 12 disposed near the focal position of the image-forming lens 11, and an image-acquisition element 13 that acquires an image of the fluorescence focused by the microlens array 12.

The operation of the thus-configured light-field microscope 1 according to this embodiment will be described below.

When a three-dimensional image of the sample X is to be acquired with the light-field microscope 1 according to this embodiment, the light source 4 of the illumination optical system 2 is made to emit excitation light. The excitation light emitted from the light source 4 and guided by the optical fiber 8 is formed in a planar shape having a certain thickness (width) as it passes through the slit 6 in the slit member 7 and enters the sample X substantially horizontally from the side.

By performing fluorescent labeling of the sample X in advance, fluorescent substances in the sample X are excited by the irradiated excitation light, generating fluorescence. The fluorescence generated in the sample X is collected by the objective lens 9, is allowed to pass through the emission filter 10 to remove the excitation light, is focused by the image-forming lens 11, and passes through the microlens array 12, and then, an image of the fluorescence is acquired by the image-acquisition element 13.

Because of the microlens array 12, the fluorescence image acquired by the image-acquisition element 13 contains not only information in the focal plane A within the sample X, but also information at the respective positions in a direction parallel to the optical axis of the objective lens 9. Hence, by performing deconvolution processing with software on the acquired fluorescence image, it is possible to extract, in an associated manner, the respective three-dimensional positions and the intensities of the fluorescence emitted from these positions and thus, it is possible to generate a three-dimensional fluorescence image of the sample X.

In this case, the light-field microscope 1 according to this embodiment makes excitation light having a predetermined thickness enter the sample X, along the focal plane A of the objective lens 9 located at a deep part in the sample X. Hence, there is an advantage that it is possible to prevent the excitation light from entering an area unnecessary for the construction of the three-dimensional image and, thus, to prevent fading of the sample X.

Specifically, because the three-dimensional-image depth is determined by the combination of the objective lens 9 and the microlens array 12, no effective information can be obtained by making excitation light enter areas located beyond that depth.

Accordingly, to efficiently acquire the fluorescence emitted within the three-dimensional-image depth, the excitation light is made to enter the minimum area including that area. By doing so, it is possible to prevent fading of the sample X, which is advantageous. When construction of a three-dimensional image having an even larger depth is desired, the focal plane A of the objective lens 9 is moved within the sample X by moving the sample X in the optical-axis direction of the objective lens 9, while maintaining the relative positions of the illumination optical system 2 and the detection optical system 3.

By doing so, it is possible to construct a three-dimensional image corresponding to the thickness of the excitation light, along a new focal plane A. In this case, because a new area has not been irradiated with the excitation light previously, the sample X has not faded. Thus, there is an advantage in that it is possible to acquire a good three-dimensional image. Furthermore, it is also possible to acquire a three-dimensional image of the entirety of the sample X by acquiring images of the sample X while sequentially moving the sample X in the optical-axis direction of the detection optical system 3 by a distance corresponding to the depth to obtain three-dimensional images and by joining them together.

Note that, in this embodiment, although the thickness of the excitation light is determined according to the three-dimensional-image depth determined by the combination of the objective lens 9 and the microlens array 12, it may be determined simply according to the combination of the objective lens 9 and the microlens array 12.

Furthermore, in this embodiment, the illumination optical system 2 radiates a static beam onto the sample X. However, if strong light-scattering particles or fluorescence absorptive particles are included inside the sample X, the excitation light may not reach to the backward of the particles in viewing from a traveling direction of the excitation light. As a result, the acquired image may have shadow. In order to suppress occurrence of shadow, the illumination optical system 2 may include a scanning means which scans the excitation light formed in a planar shape in the plane thereof to radiate the excitation light onto the sample X in different angles around the axis of the detection optical system 3.

Next, a light-field microscope 14 according to a second embodiment of the present invention will be described below with respect to FIG. 2.

In the description of this embodiment, parts having configurations common to those of the light-field microscope 1 according to the above-described first embodiment will be denoted by the same reference signs, and descriptions thereof will be omitted.

Figure 2:
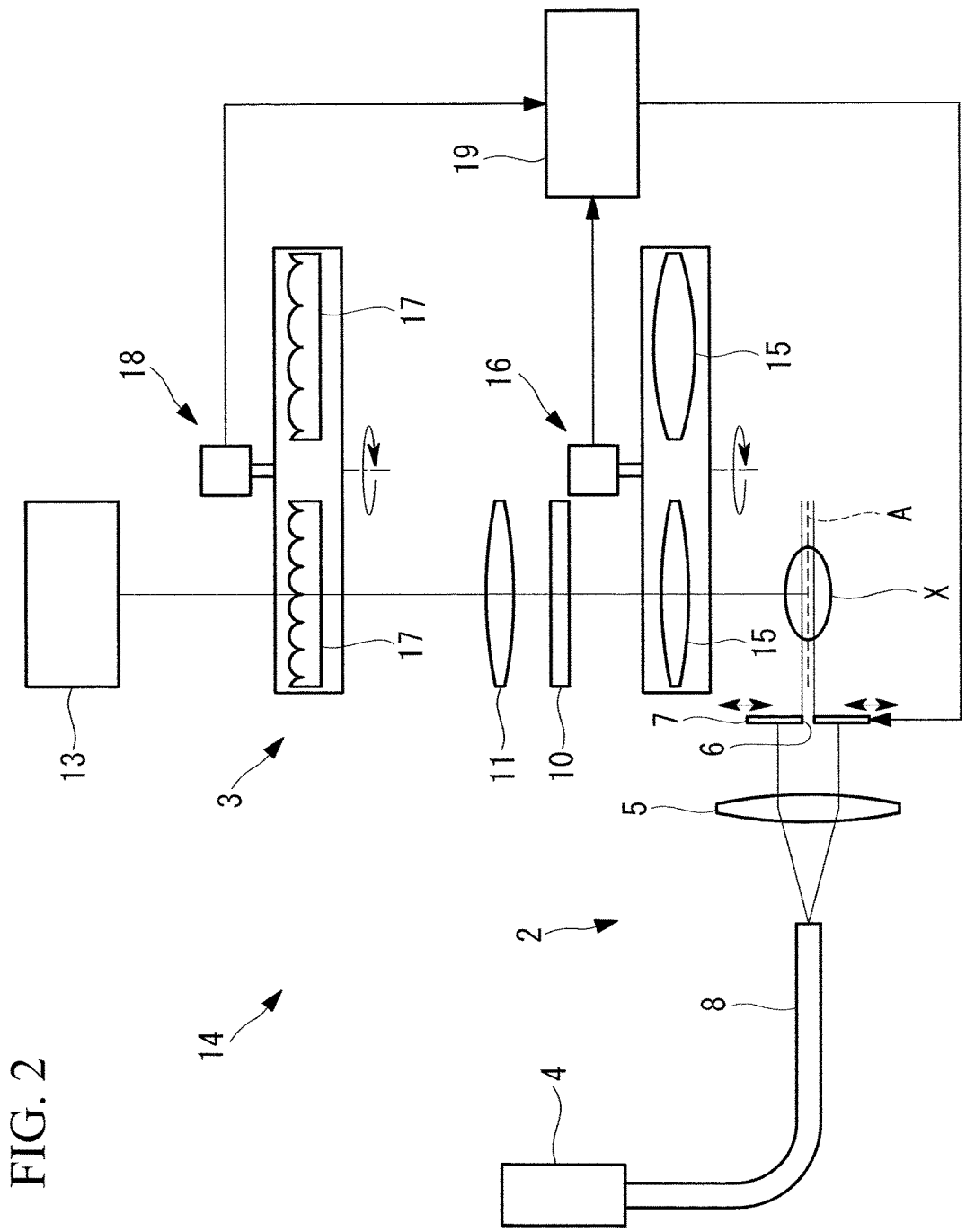
FIG. 2 is a schematic diagram showing the overall configuration of a light-field microscope according to a second embodiment of the present invention.

As shown in FIG. 2, a light-field microscope 14 according to this embodiment differs from the light-field microscope 1 according to the first embodiment in that the opening width of the slit 6 in the slit member 7 is adjustable and in that it includes a plurality of objective lenses 15 having different magnifications, a revolver 16 for changing the objective lenses 15, a plurality of microlens arrays 17 having different lens pitches, a turret 18 for selectively positioning one of the microlens arrays 17 in the optical path, and a controller 19 that controls the slit member 7 according to the combination of the objective lens 15 and the microlens array 17.

The revolver 16 and the turret 18 are provided with sensors (not shown), which transmit the types of the objective lens 15 and the microlens array 17 located on the optical axis to the controller 19.

In the thus-configured light-field microscope 14 according to this embodiment, in order to obtain the intended three-dimensional-image depth, an objective lens 15 with any magnification is selected from the plurality of objective lenses 15 having different magnifications and is disposed in the optical axis by operating the revolver 16, and a microlens array 17 with any pitch is selected from the microlens arrays 17 having different pitches and is disposed in the optical axis by operating the turret 18.

Because the sensor provided on the revolver 16 detects the magnification of the objective lens 15 disposed in the optical axis, and the sensor provided on the turret 18 detects the pitch of the microlens array 17 disposed in the optical axis, the controller 19 determines the three-dimensional-image depth on the basis of the selected magnification of the objective lens 15 and pitch of the microlens array 17 and adjusts the opening width of the slit 6 in the slit member 7 so that excitation light having a thickness corresponding to the determined depth is radiated onto the sample X.

With this configuration, when an observer selects a desired objective lens 15 and microlens array 17 according to the necessary image-acquisition magnification and resolution, it is possible to radiate excitation light having a most suitable thickness for the combination of the selected objective lens 15 and microlens array 17 onto the sample X. Hence, it is possible to prevent radiation of the excitation light onto an unnecessary area, leading to an advantage in that it is possible to effectively prevent fading of the sample X.

Figure 3:
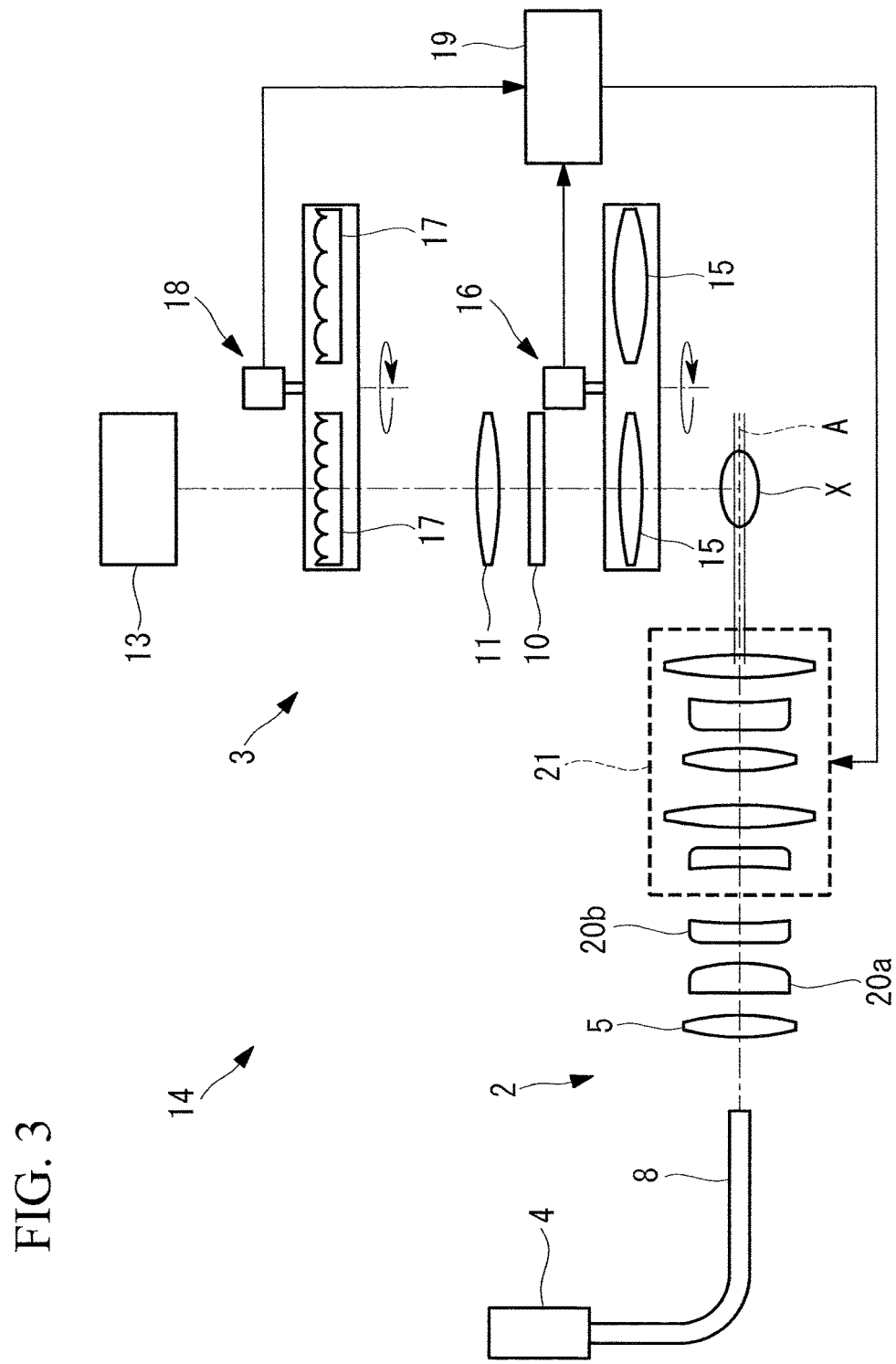
FIG. 3 is a schematic diagram showing the overall configuration of a first modification of the light-field microscope in FIG. 2.

Note that, in this embodiment, although the thickness of the excitation light radiated onto the sample X is adjusted by changing the opening width of the slit 6 in the slit member 7, instead, a configuration like that shown in FIG. 3 is also possible, in which excitation light emitted from the optical fiber 8 of the illumination optical system 2 is formed in a flat planar shape with the collimating lens 5 and cylindrical lenses 20a and 20b, and the excitation light formed in this shape is allowed to enter a zoom optical system (beam-width adjuster) 21, and the zoom optical system 21 continuously changes the thickness of the excitation light radiated onto the sample X.

Figure 4:
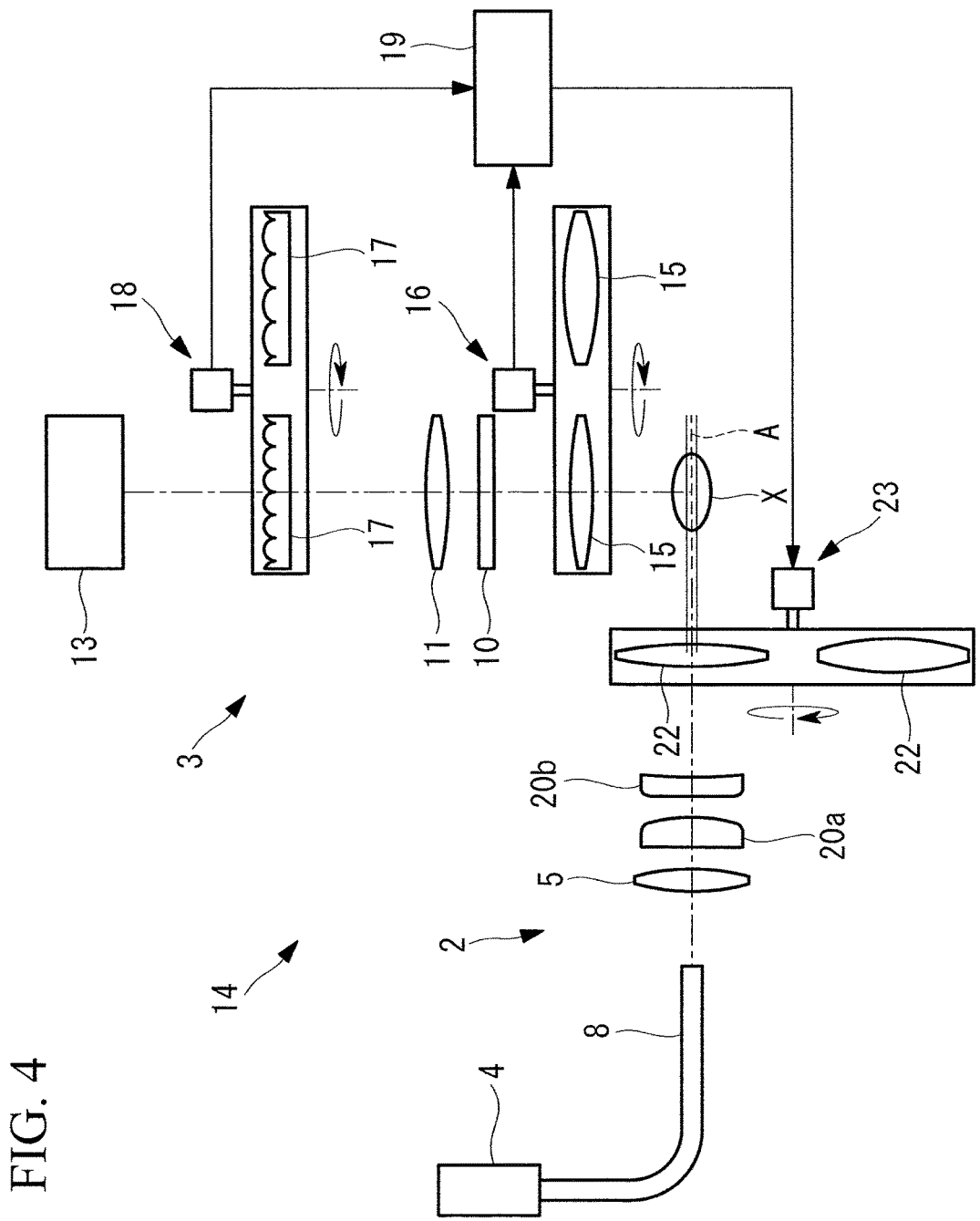
FIG. 4 is a schematic diagram showing the overall configuration of a second modification of the light-field microscope in FIG. 2.

Alternatively, as show in FIG. 4, a turret (beam-width adjuster) 23 that can selectively dispose one of a plurality of beam expanders (optical systems) 22 having different magnifications between the cylindrical lens 20b and the sample X may be employed instead of the zoom optical system 21. This makes it possible to gradually change the thickness of the excitation light radiated onto the sample X.

Figure 5:
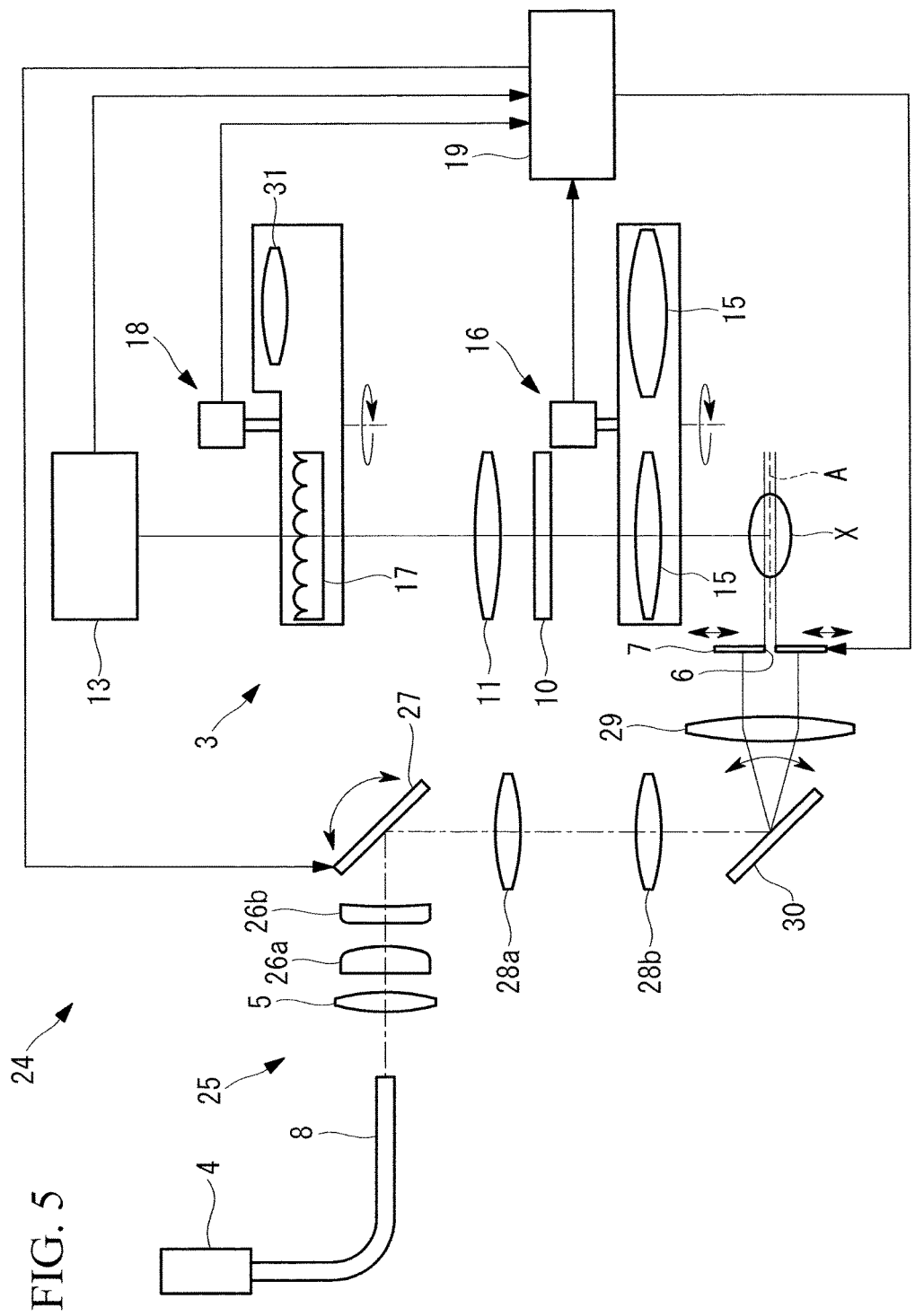
FIG. 5 is a schematic diagram showing the overall configuration of a light-field microscope according to a third embodiment of the present invention, showing a state in which a microlens array is disposed in the optical axis of an objective lens.

Next, a light-field microscope 24 according to a third embodiment of the present invention will be described with reference to FIG. 5 and FIG. 6.

In the description of this embodiment, parts having configurations common to those of the light-field microscope 14 according to the above-described second embodiment will be denoted by the same reference signs, and descriptions thereof will be omitted.

The light-field microscope 24 according to this embodiment differs from the light-field microscope 14 according to the second embodiment in that it includes an illumination optical system 25 and in that one of the microlens array 17 and a relay lens 31 is selectively provided between the image-forming lens 11 and the image-acquisition element 13 in such a manner as to be insertable therein and removable therefrom.

The illumination optical system 25 includes: the light source 4 (sheet-illumination-light generator); a galvanometer mirror (scanner) 27 that one-dimensionally scans excitation light formed in a sheet shape by the collimating lens (sheet-illumination-light generator) 5 and cylindrical lenses (sheet-illumination-light generators) 26a and 26b; relay lenses 28a and 28b; and a light-focusing lens 29 that changes the exit angle, which is varied by the scanning performed by the galvanometer mirror 27, into a substantially horizontal angle. Furthermore, the slit member (opening-width changer) 7 is provided behind the light-focusing lens 29 to make only a portion of the excitation light at substantially the central portion of the scanning area of the galvanometer mirror 27 pass therethrough and enter the sample X. In FIG. 5, reference sign 30 denotes an optical-path forming mirror.

The operation of the thus-configured light-field microscope 24 according to this embodiment will be described below.

The excitation light emitted from the optical fiber 8 is formed in a thin parallel light beam by the collimating lens 5 and the cylindrical lenses 26a and 26b, is scanned by the galvanometer mirror 27, is relayed by the relay lenses 28a and 28b, is focused by the light-focusing lens 29, passes through the slit member 7, and is radiated on the sample X.

The focal position of the light-focusing lens 29 is located substantially on the optical axis of the objective lens 15. Hence, the sheet-shaped excitation light entering the sample X along a plane substantially perpendicular to the optical axis of the objective lens 15 is focused in the optical axis direction and has the minimum thickness near the optical axis of the objective lens 15. The sheet-shaped excitation light formed in this manner is scanned in the optical-axis direction of the objective lens 15 by the oscillation of the galvanometer mirror 27.

The excitation-light scanning speed of the galvanometer mirror 27 is sufficiently higher than the exposure time of the image-acquisition element 13, and the scanning corresponding to at least the opening width of the slit 6 can be performed within the exposure time.

Hence, similarly to the case where the excitation light having a thickness determined by the opening width of the slit 6 is radiated, a fluorescence signal for acquiring a three-dimensional image can be acquired also with sheet-shaped excitation light that is sufficiently thinner than the opening width of the slit 6.

It is desirable that the driving waveform be a sine wave when the galvanometer mirror 27 is oscillated at a high speed. In this case, the angular velocity of the sine wave with respect to the scanning angle of the galvanometer mirror 27 is not uniform. In this embodiment, by limiting, by means of the slit member 7, the excitation light to be emitted to the sample X to that at the center and the vicinity of the scanning area of the galvanometer mirror 27, it is possible to scan the sheet-shaped excitation light over the sample X artificially at a constant speed. The slit member 7 is preferably disposed near the sample X or disposed at or near the focal position of the relay lenses 28a.

Note that the scanning speed may be corrected by, for example, modulating the excitation light with a modulator, such as an acoustooptic modulator, before the excitation light is made to enter the optical fiber 8.

Figure 6:
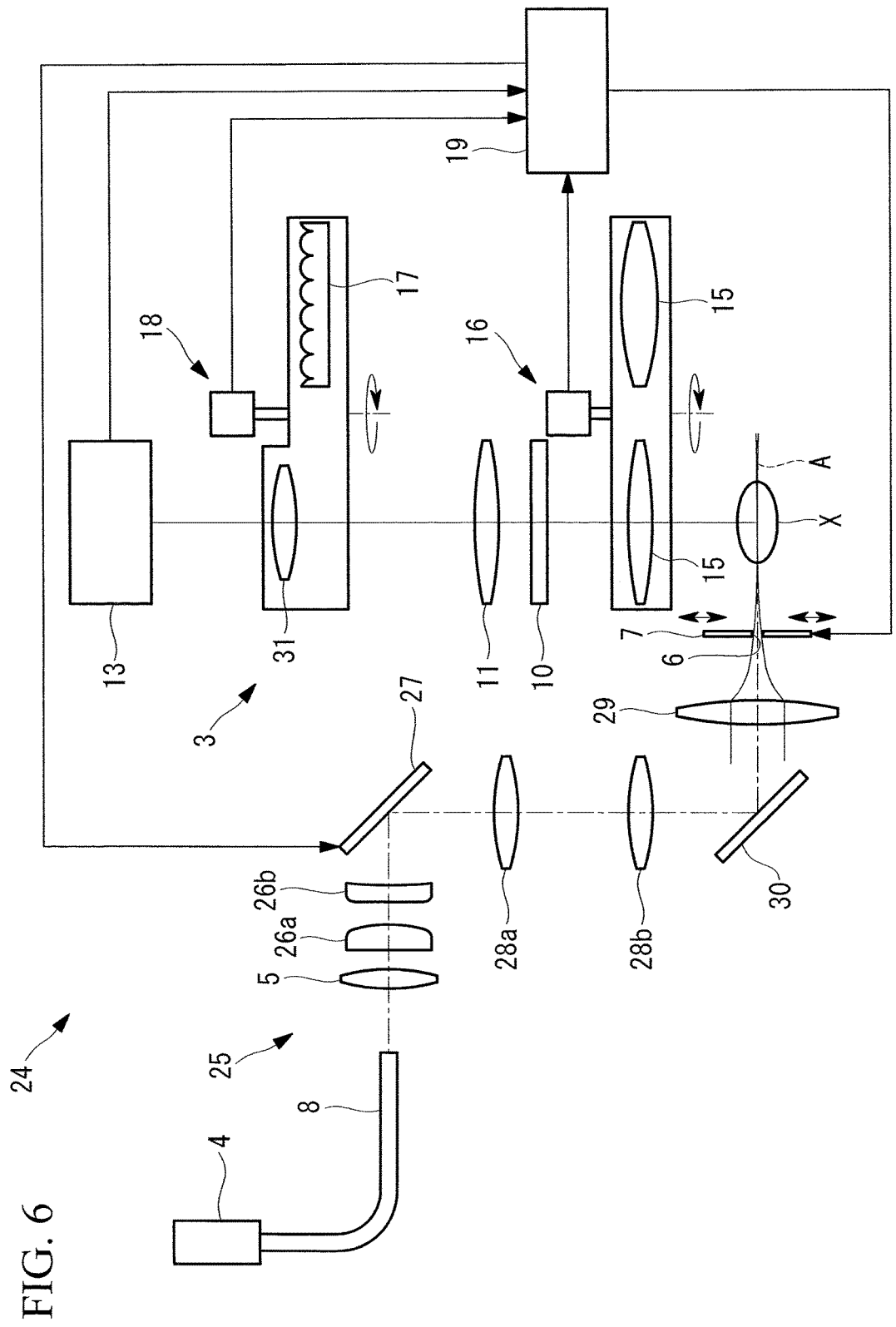
FIG. 6 is a schematic diagram showing the overall configuration of the light-field microscope according to the third embodiment of the present invention, showing a state in which the microlens array is removed from the optical axis of the objective lens.

Furthermore, as shown in FIG. 6, the light-field microscope 24 according to this embodiment may be used as a sheet-illumination microscope by stopping scanning with the galvanometer mirror 27 and fixing the sheet-shaped excitation light to a position parallel to the focal plane A of the objective lens 15, and by removing the microlens array 17 from the optical axis and inserting the relay lens 31 into the optical path. An observer can switchably use the light-field microscope 24 and the sheet-illumination microscope according to the purpose. In this embodiment, the light-field microscope 24 and the sheet-illumination microscope are switchably used by selecting a scanning state or non-scanning state of the sheet-shaped excitation light having a focal point. Alternatively, for example, an asymmetric optical element, such as a cylindrical lens, may be inserted into or removed from the optical path of the thin parallel light beam. By doing so, the light-field microscope 24 and the sheet-illumination microscope can be also switchably used.

Furthermore, a parallel flat glass may be disposed, instead of the relay lens 31, as a means for correcting an imaging position when switching to the sheet-illumination microscope.

Furthermore, in the light-field microscope 24 according to this embodiment, because sufficiently thin sheet-shaped excitation light is radiated onto the sample X, ultrashort-pulsed laser light may be used as excitation light to cause fluorescence to be generated by multiphoton absorption effect.

Furthermore, the sheet-shaped excitation light may be linear light beam which is focused substantially at the optical axis of the objective lens 15 and which is scanned toward the in-plain direction of the sheet-shaped excitation light. By doing so, light density at the focusing position can be increased and therefore fluorescence can be generated by higher multiphoton absorption effect.

Furthermore, similarly to the second embodiment, the opening width of the slit 6 in the slit member 7 may be adjusted according to the combination of the magnification of the objective lens 15 and the pitch of the microlens array 17.

The following aspects of the invention are derived from the embodiments described above.

An aspect of the present invention is a light-field microscope including: an illumination optical system that radiates excitation light onto a sample; and a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens, wherein the illumination optical system radiates a beam of the excitation light having a predetermined width in the optical-axis direction of the objective lens so as to include the focal plane of the objective lens onto the sample in a direction substantially perpendicular to the optical axis.

In this aspect, when the illumination optical system radiates excitation light onto the sample, the fluorescence generated in the sample is collected by the objective lens, passes through the microlens array, and then, an image of the fluorescence is acquired by the image-acquisition element. With this configuration, not only information in the focal plane of the objective lens in the sample, but also information at the respective portions of the sample through which the excitation light has passed can be acquired with the image-acquisition element. Hence, a three-dimensional image of the sample can be acquired on the basis of the acquired image information.

In this case, because the illumination optical system radiates a beam of the excitation light having a predetermined width in the optical-axis direction of the objective lens onto the sample in a direction substantially perpendicular to the optical axis, it is possible to efficiently radiate the excitation light onto an area necessary for acquiring a three-dimensional image of the sample, and thus, it is possible to prevent fading of the sample in other areas. Accordingly, even when observation is performed at a position where the focal plane has been shifted in the optical-axis direction of the objective lens, because the sample has not faded, a good three-dimensional image of the sample can be acquired.

In the above-described aspect, the illumination optical system may include a beam-width adjuster that changes the beam width of the excitation light.

With this configuration, by adjusting the beam width of the excitation light by actuating the beam-width adjuster, it is possible to radiate the excitation light onto only the necessary area according to the three-dimensional-image depth determined by the combination of the objective lens and the microlens array and to suppress fading of the sample.

Furthermore, in the above-described aspect, images may be acquired while sequentially moving the sample in the optical axis direction of the detection optical system by a predetermined distance determined by the combination of the objective lens and the microlens array.

Furthermore, in the above-described aspect, the illumination optical system may include a light source that emits the excitation light, and a slit that allows a portion of the excitation light from the light source to pass therethrough, and the beam-width adjuster may change the opening width of the slit.

With this configuration, as a result of the beam-width adjuster changing the opening width of the slit, it is possible to easily adjust the beam width of the excitation light that is made to enter the sample.

Furthermore, in the above-described aspect, the illumination optical system may include a light source that emits the excitation light, and a zoom optical system that focuses the excitation light from the light source, and the beam-width adjuster may change the zoom magnification of the zoom optical system.

With this configuration, as a result of the beam-width adjuster changing the zoom magnification of the zoom optical system, it is possible to easily adjust the beam width of the excitation light that is made to enter the sample.

Furthermore, in the above-described aspect, the illumination optical system may include a light source that emits the excitation light, and a plurality of optical systems having different magnifications and selectively inserted into the optical path of the excitation light emitted from the light source to focus the excitation light, and the beam-width adjuster may switch among the plurality of optical systems.

With this configuration, as a result of the beam-width adjuster selectively switching among the optical systems having different magnifications, it is possible to easily adjust the beam width of the excitation light that is made to enter the sample.

Furthermore, in the above-described aspect, at least one of the objective lens and the microlens array may be provided in a switchable manner, and a controller that controls the beam-width adjuster when at least one of the objective lens and the microlens array is switched may be provided.

With this configuration, it is possible to adjust, by means of the controller, the beam width of the excitation light to an appropriate beam width for radiating the excitation light only onto the necessary area according to the three-dimensional-image depth determined by the combination of the objective lens and the microlens array and, thus, to suppress fading of the sample.

Furthermore, another aspect of the present invention is a light-field microscope including: an illumination optical system that radiates excitation light onto a sample; and a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens, wherein the illumination optical system includes a sheet-illumination-light generator that generates a sheet-shaped beam extending parallel to a direction substantially perpendicular to the optical axis of the objective lens and that radiates the beam onto the sample in a direction substantially perpendicular to the optical axis, and a scanner that scans the sheet-shaped beam generated by the sheet-illumination-light generator in the optical axis direction, over a predetermined area including the focal plane of the objective lens, within the exposure time for one image in the image-acquisition element.

With this aspect, by scanning the sheet-shaped beam, which is generated by the sheet-illumination-light generator and is to be radiated onto the sample along a direction substantially perpendicular to the optical axis of the objective lens, in the optical axis direction by actuating the scanner, it is possible to obtain the same effect as in the case where excitation light having a width of the predetermined area including the focal plane is radiated.

In the above-described aspect, at least one of the objective lens and the microlens array may be provided in a switchable manner, and a controller that controls the scanning width of the sheet-shaped beam in the scanner when at least one of the objective lens and the microlens array is switched may be provided.

With this configuration, it is possible to radiate, by means of the controller, the excitation light only onto the necessary area according to the three-dimensional-image depth determined by the combination of the objective lens and the microlens array and, thus, to suppress fading of the sample.

Furthermore, in the above-described aspect, a slit having an opening width may be provided at a portion of the scanning width over which the sheet-shaped beam is scanned by the scanner.

With this configuration, because there is an area in which the scanning speed is substantially constant near the center of the scanning width over which the sheet-shaped beam is scanned by the scanner, it is possible to extract solely the sheet-shaped beam scanned at a constant speed and radiate it onto the sample.

Furthermore, in the above-described aspect, an opening-width changer that changes the opening width of the slit may be provided.

With this configuration, it is possible to radiate the excitation light only onto the necessary area according to the three-dimensional-image depth determined by the combination of the objective lens and the microlens array and, thus, to suppress fading of the sample.

Furthermore, in the above-described aspect, the excitation light may be ultrashort-pulsed laser light.

With this configuration, it is possible to cause fluorescence to be generated in the sample due to multiphoton absorption effect.

Furthermore, in the above-described aspect, the microlens array and the relay lens may be selectively provided between the image-acquisition element and the objective lens in such a manner as to be insertable therein and removable therefrom.

With this configuration, while it is possible to acquire a three-dimensional image of the sample by inserting the microlens array, it is possible to acquire a two-dimensional image extending along the sheet-shaped beam by removing the microlens array from and inserting the relay lens into the optical path and by stopping the scanner and fixing the sheet-shaped beam near the focal plane of the objective lens.

REFERENCE SIGNS LIST 1, 14, 24 light-field microscope
2, 25 illumination optical system
3 detection optical system
4 light source (sheet-illumination-light generator)
5 collimating lens (sheet-illumination-light generator)
6 slit
7 slit member (beam-width adjuster, opening-width changer)
9, 15 objective lens
12, 17 microlens array
13 image-acquisition element
19 controller
21 zoom optical system (beam-width adjuster)
22 beam expander (optical system)
26a and 26b cylindrical lens (sheet-illumination-light generator)
27 galvanometer mirror (scanner)
A focal plane
X sample

The invention claimed is:

1. A light-field microscope comprising:
an illumination optical system that radiates excitation light onto a sample;
a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens; and
a processor configured to generate a three-dimensional fluorescence image of the sample based on a single fluorescence image acquired by the image-acquisition element,
wherein the illumination optical system radiates a beam of the excitation light onto the sample in a direction substantially perpendicular to an optical axis of the objective lens, the beam having a predetermined beam width in a direction of the optical axis, and the predetermined beam width including a focal plane of the objective lens and being adapted to a depth of the three-dimensional fluorescence image.

2. The light-field microscope according to claim 1, wherein the illumination optical system includes a beam-width adjuster that changes the predetermined beam width of the excitation light.

3. The light-field microscope according to claim 2, wherein:
the illumination optical system includes a light source that emits the excitation light, and a slit that allows a portion of the excitation light from the light source to pass therethrough, and
the beam-width adjuster changes an opening width of the slit.

4. The light-field microscope according to claim 2, wherein:
the illumination optical system includes a light source that emits the excitation light, and a zoom optical system that focuses the excitation light from the light source, and
the beam-width adjuster changes a zoom magnification of the zoom optical system.

5. The light-field microscope according to claim 2, wherein:
the illumination optical system includes a light source that emits the excitation light, and a plurality of optical systems having different magnifications and being selectively insertable into an optical path of the excitation light emitted from the light source to focus the excitation light, and
the beam-width adjuster switches among the plurality of optical systems.

6. The light-field microscope according to claim 2, further comprising:
a switching mechanism configured to switch at least one of the objective lens and the microlens array to a different type thereof; and
a controller that controls the beam-width adjuster according to the type of the at least one of the objective lens and the microlens array.

7. The light-field microscope according to claim 1, wherein images are acquired while the sample is sequentially moved in the direction of the optical axis by a predetermined distance determined based on a combination of a type of the objective lens and a type of the microlens array.

8. The light-field microscope according to claim 1, wherein the processor is configured to perform deconvolution processing on the single fluorescence image acquired by the image-acquisition element to generate the three-dimensional fluorescence image of the sample.

9. A light-field microscope comprising:
an illumination optical system that radiates excitation light onto a sample;
a detection optical system including an objective lens that collects fluorescence generated in the sample as a result of the sample being irradiated with the excitation light by the illumination optical system, an image-acquisition element that acquires an image of the fluorescence collected by the objective lens, and a microlens array disposed between the image-acquisition element and the objective lens; and
a processor configured to generate a three-dimensional fluorescence image of the sample based on a single fluorescence image acquired by the image-acquisition element,
wherein the illumination optical system includes:
a sheet-illumination-light generator that generates a sheet-shaped beam extending parallel to a direction substantially perpendicular to an optical axis of the objective lens and that radiates the beam onto the sample in a direction substantially perpendicular to the optical axis; and
a scanner that scans the sheet-shaped beam generated by the sheet-illumination-light generator in the optical axis direction, over a predetermined area including a focal plane of the objective lens and being adapted to a depth of the three-dimensional fluorescence image, within an exposure time for acquiring the single fluorescence image by the image-acquisition element.

10. The light-field microscope according to claim 9, further comprising:
a switching mechanism configured to switch at least one of the objective lens and the microlens array to a different type thereof; and
a controller that controls a scanning width of the sheet-shaped beam in the scanner according to the type of the at least one of the objective lens and the microlens when the at least one of the objective lens and the microlens array is switched.

11. The light-field microscope according to claim 9, further comprising a slit provided behind the scanner,
wherein the slit has an opening width through which only a portion of a scanning area of the excitation light scanned by the scanner is passed.

12. The light-field microscope according to claim 11, further comprising an opening-width changer that changes the opening width of the slit.

13. The light-field microscope according to claim 9, wherein the excitation light is ultrashort-pulsed laser light.

14. The light-field microscope according to claim 9, further comprising a switching mechanism configured to selectively insert the microlens array and a relay lens into an optical path of the detection optical system.

15. The light-field microscope according to claim 9, further comprising a switching mechanism configured to selectively insert the microlens array and an imaging-position correcting element into an optical path of the detection optical system.

16. The light-field microscope according to claim 9, wherein the processor is configured to perform deconvolution processing on the single fluorescence image acquired by the image-acquisition element to generate the three-dimensional fluorescence image of the sample.

17. An imaging method in a light-field microscope including an illumination optical system, an objective lens that collects fluorescence generated in a sample as a result of the sample being irradiated with excitation light by the illumination optical system, an image-acquisition element that acquires an image of the fluorescence collected by the objective lens, and a microlens array disposed between the image-acquisition element and the objective lens, the method including:
radiating, by the illumination optical system, a beam of the excitation light onto the sample in a direction substantially perpendicular to an optical axis of the objective lens, the beam having a predetermined beam width in a direction of the optical axis, and the predetermined beam width including a focal plane of the objective lens and being adapted to a depth of a three-dimensional fluorescence image of the sample;
acquiring, by the image-acquisition element, a single fluorescence image of fluorescence generated in the sample during the radiating; and
generating the three-dimensional fluorescence image of the sample based on the single fluorescence image acquired in the acquiring.

18. The method according to claim 17, the method further including:
adjusting the predetermined beam width according to a type of at least one of the objective lens and the microlens array.

19. The method according to claim 17, wherein the generating generates the three-dimensional fluorescence image of the sample by performing deconvolution processing on the single fluorescence image acquired in the acquiring.

20. An imaging method in a light-field microscope including an illumination optical system, an objective lens that collects fluorescence generated in a sample as a result of the sample being irradiated with excitation light by the illumination optical system, an image-acquisition element that acquires an image of the fluorescence collected by the objective lens, and a microlens array disposed between the image-acquisition element and the objective lens, the method including:
radiating, by the illumination optical system, a sheet-shaped beam, which is focused near an optical axis of the objective lens and which extends parallel to a direction substantially perpendicular to the optical axis, onto the sample in a direction substantially perpendicular to the optical axis;
scanning, by the illumination optical system, the sheet-shaped beam in the optical axis direction, over a predetermined area including a focal plane of the objective lens and being adapted to a depth of a three-dimensional fluorescence image, within an exposure time for acquiring one image the image-acquisition element;
acquiring, by the image-acquisition element, a single fluorescence image of fluorescence generated in the sample during the scanning; and
generating the three-dimensional fluorescence image of the sample based on the single fluorescence image acquired in the acquiring.

21. The method according to claim 20, further including:
controlling a scanning width of the sheet-shaped beam in the optical axis direction according to a type of at least one of the objective lens and the microlens array.

22. The method according to claim 20, wherein ultrashort-pulsed laser light is used as the excitation light.

23. The method according to claim 20, wherein the generating generates the three-dimensional fluorescence image of the sample by performing deconvolution processing on the single fluorescence image acquired in the acquiring.

* * * * *